(12) United States Patent
Alfano et al.

(10) Patent No.: US 6,208,886 B1
(45) Date of Patent: Mar. 27, 2001

(54) NON-LINEAR OPTICAL TOMOGRAPHY OF TURBID MEDIA

(75) Inventors: Robert R. Alfano, Bronx; Yici Guo, Jackson Height; Feng Liu, Bronx; Ping Pei Ho, Great Neck, all of NY (US)

(73) Assignee: The Research Foundation of City College of New York, New York, NY (US)

( * ) Notice: Subject to any disclaimer, the term of this patent is extended or adjusted under 35 U.S.C. 154(b) by 0 days.

(21) Appl. No.: 09/054,743

(22) Filed: Apr. 3, 1998

Related U.S. Application Data

(60) Provisional application No. 60/042,645, filed on Apr. 4, 1997.

(51) Int. Cl.$^7$ .......................................................... A61B 5/00
(52) U.S. Cl. ........................ 600/473; 356/432; 250/341.1; 250/358.1
(58) Field of Search .................................... 600/310, 473, 600/476; 356/446, 436, 432, 441, 239, 240; 250/341.1, 358.1

(56) References Cited

U.S. PATENT DOCUMENTS

| | | | |
|---|---|---|---|
| 5,034,613 | * 7/1991 | Denk et al. | 250/458.1 |
| 5,371,368 | * 12/1994 | Alfano et al. | 150/341.1 |
| 5,699,798 | * 12/1997 | Hochman et al. | 128/653.1 |
| 5,813,987 | * 9/1998 | Modell et al. | 600/473 |
| 5,813,988 | * 9/1998 | Alfano et al. | 600/476 |
| 5,865,754 | * 2/1999 | Sevick-Muraca et al. | 600/476 |
| 5,999,836 | * 9/1998 | Nelson et al. | 600/407 |

OTHER PUBLICATIONS

Guo et al., "Optical harmonic generation from animal tissues by the use of picosecond and femtosecond laser pulses," Appl. Opt. 35(34):6810–3 (Dec. 1, 1996).

Guo et al., "Two–photon excitation of fluorescence from chicken tissue," Appl. Opt., 36(4):968–70 (Feb. 1, 1997).

Guo et al., "Second–harmonic tomography of tissues," Opt. Lett., 22(17):1323–5, (Mar. 3, 1997).

Denk et al., "Two–Photon Excitation in Functional Biological Imaging," J. Biomed. Opt., 1:296–304 (Jul. 1996).

Fine et al., "Optical Second Harmonic Generation in Biological Systems," Appl. Opt., 10:2350–3 (1971).

Heinz et al., "Spectroscopy of Molecular Monolayers by Resonant Second–Harmonic Generation," Phys. Rev. Lett., 48:478–51 (1982).

(List continued on next page.)

* cited by examiner

*Primary Examiner*—Francis J. Jaworski
*Assistant Examiner*—Eleni Mantis Mercader
(74) *Attorney, Agent, or Firm*—Kriegsman & Kriegsman

(57) ABSTRACT

An apparatus utilizing non-linear optical signals for use in constructing a three-dimensional tomographic map of an in vivo biological tissue for medical disease detection purposes. In one embodiment, said apparatus comprises a stage for supporting the in vivo biological tissue; a laser for illuminating the in vivo biological tissue with a focused beam of laser light, the light emerging from the in vivo biological tissue comprising fundamental light, harmonic wave light, and fluorescence due to multi-photon excitation; a filter for selectively passing only at least one of the harmonic wave light and the fluorescence; one or more detectors for individually detecting each of the harmonic wave light and the fluorescence selectively passed; and a mechanism for moving the laser relative to the stage in x, y and z directions.

37 Claims, 16 Drawing Sheets

OTHER PUBLICATIONS

Gannaway et al., "Second–harmonic imaging in the scanning optical microscope," Optical and Quantum Electronics, 10:435–9 (1978).

Huang et al., "Optical Coherence Tomography," Science, 254:1178–81 (1991).

Freund et al., "Connective Tissue Polarity," Biophys. J., 50:693–712 (1986).

Benaron et al., "Optical Time–of–Flight and Absorbance Imaging of Biological Media," Science, 259:1463–6 (1993).

Wang et al., "Ballistic 2–D Imaging Through Scattering Walls Using an Ultrafast Optical Kerr Gate," Science, 253:769–71 (1991).

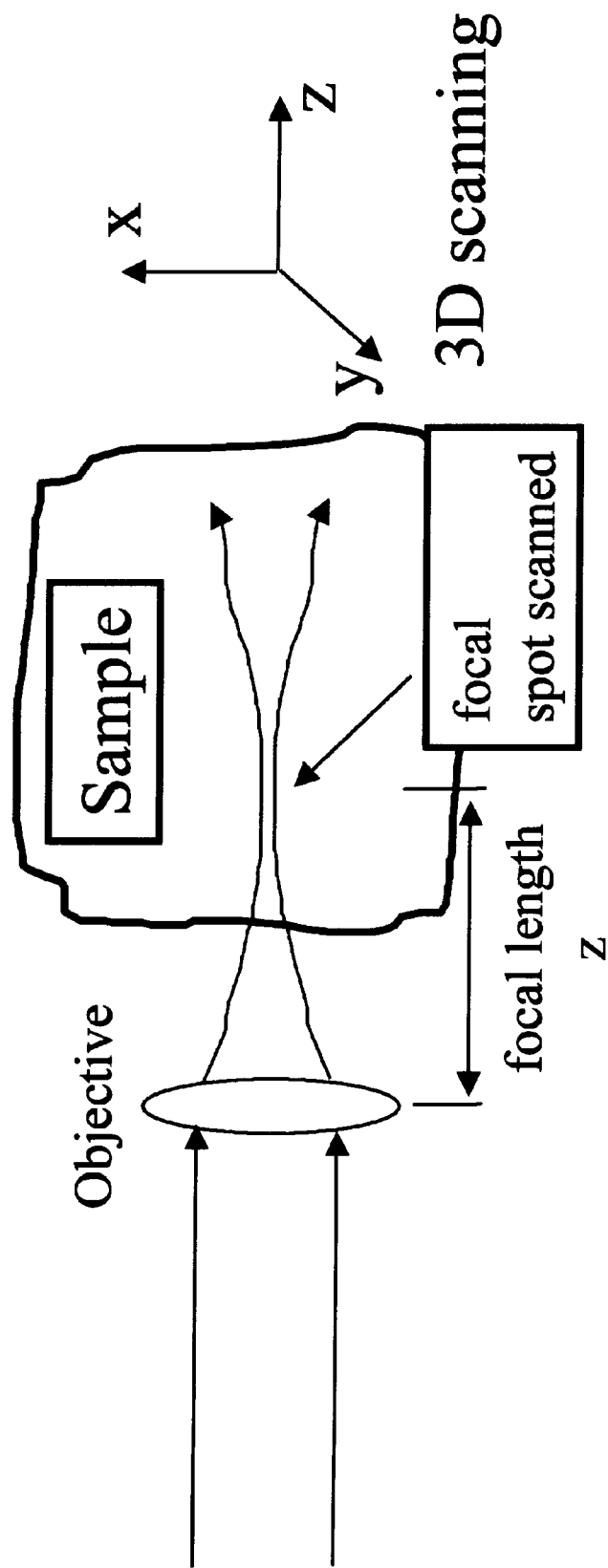
Fig. 1(a)  Inset

F1 and F2 Bandpass Filters for
SHG and TPF detection, respectively

Imaging setup without moving sample

NON-LINEAR OPTICAL TOMOGRAPHY OF TURBID MEDIA

CROSS-REFERENCE TO RELATED APPLICATIONS

The present application claims the benefit under 35 U.S.C. 119(e) of U.S. Provisional Patent Application Serial No. 60/042,645, filed Apr. 4, 1997, the disclosure of which is incorporated herein by reference.

BACKGROUND OF THE INVENTION

The present relates generally to the imaging of turbid (i.e., highly scattering) media and more particulary to a novel method and apparatus for the three-dimensional imaging of turbid media, such as biological tissues.

Optical imaging and microscopy have attracted considerable attention because of their potential in the development of non-invasive medical diagnostic modalities. See e.g., Huang et al., Science 254, 1178 (1991); Piston et al., J. Microsc., 178, 20 (1994); Freund et al., Biophys. J., 50, 693 (1986); Benaron et al., Science, 259, 1463 (1993); and Wang et al., Science, 253, 769 (1991), all of which are incorporated herein by reference. Achieving high spatial resolution remains one of the top priorities for precisely localizing biological structures and changes in the state of tissues at different locations. Some of the powerful in vitro and in vivo imaging techniques developed for highly turbid media, to-date, include optical coherence tomography (OCT), time of flight and Fourier-Kerr gate imaging methods, with micrometer to sub-millimeter spatial resolutions. Imaging techniques that use nonlinear-optical effects have been demonstrated to have an additional advantage in spatial resolution, owing to a higher-order dependence on the excitation intensity. Submicrometer lateral resolution has been achieved in three dimensions in the detection of cellular metabolism in the rabbit cornea, through two-photon excitation of fluorescence (TPF) from reduced pyridine nucleotides. A combination of confocal linear-optical approaches and TPF has also been used as an alternative for visualizing the structure of biological tissues. See Denk, J. Biomed. Opt., 1, 296 (1996), which is incorporated herein by reference; see also U.S. Pat. No. 5,034,613, inventors Denk et al., which issued Jul. 23, 1991, and which is incorporated herein by reference.

Second-harmonic generation (SHG) in nearly transparent tissues was first disclosed in Fine et al., Appl. Opt., 10, 2350 (1971), which is incorporated herein by reference. Cross-beam-scanning SHG microscopy was studied with a transmission geometry to show detailed variation of collagenous filaments in a rat tail tendon. Recently, a correlation of second-harmonic signal strength with tissue structure in native chicken tissues was disclosed in Guo et al., "Optical harmonic generation from animal tissues by the use of picosecond and femtosecond laser pulses," Appl. Opt., 35, 6810 (1996), which is incorporated herein by reference. See also Guo et al., "Two photon excitation of fluorescence from chicken tissue," Appl. Opt., 36, 968–970 (1997), which is incorporated herein by reference. In terms of spatial resolution, second-harmonic tomography is identical to two-photon microscopy, in which the localization effect is based on quadratic dependence of the signal on the input photon density. However, an advantage of using an infrared excitation source in second-harmonic tomography is its deeper penetration depth and the fact that it generates less photobleaching and causes less damage than a single-photon-fluorescence confocal microscopy. In contrast with TPF, second-harmonic generation has the advantage that contrast can be obtained from nonfluorescent samples and tissues. An inverse higher-order dependence of second-harmonic intensity on the refractive index allows one to highlight small changes in reflectance. The second-harmonic signal arises from the second-order nonlinear-optical susceptibility $\chi^2$ tensor, which depends on the electronic configuration, molecular symmetry, local morphology, orientation, and alignment of the molecules and ultrastructures. The potential of using second-harmonic generation to determine symmetry properties of the local environment and surfaces in homogeneous and amorphous media has been demonstrated in Heinz et al., Phys. Rev. Lett., 48, 478 (1982), which is incorporated herein by reference. The excitation wavelength of second-harmonic generation is not restricted to the absorption band of the molecules and thus can be further extended toward the infrared region. This property is in contrast with multiphoton microscopy, in which extending the source wavelength is accompanied by a trade-off in the signal magnitude, through a three-photon or even higher-order process. Second-harmonic generation is a second-order nonlinear-optical process that can generate signals that are orders of magnitude higher than that from a third-order process (TPF), permitting signal detection from deeper in the scattering medium.

SUMMARY OF THE INVENTION

It is an object of the present invention to provide a new method and apparatus for the three-dimensional imaging of turbid media, such as biological tissues.

It is another object of the present invention to provide a method and apparatus as described above that are well-suited for use with in vivo biological tissues.

It is yet another object of the present invention to provide a method and apparatus as described above that utilize non-linear optical signals, such as second or higher-order harmonic generation and/or fluorescence due to multi-photon (i.e., two or more photon) excitation.

According to one aspect of the invention, there is provided an apparatus utilizing non-linear optical signals for use in constructing a three-dimensional tomographic map of an in vivo biological tissue for medical disease detection purposes, said apparatus comprising (a) means for supporting said in vivo biological tissue; (b) means for illuminating said in vivo biological tissue with a focused beam of laser light, said light emerging from said in vivo biological tissue comprising fundamental light, harmonic wave light, and fluorescence due to multi-photon excitation; (c) means for selectively passing only at least one of said harmonic wave light and said fluorescence; (d) means for individually detecting each of said harmonic wave light and said fluorescence selectively passed; and (e) means for moving said illuminating means relative to said supporting means in x, y and z directions.

According to another aspect of the invention, there is provided a method utilizing non-linear optical signals for use in constructing a three-dimensional tomographic map of an in vivo biological tissue for medical disease detection purposes, said method comprising the steps of (a) providing an in vivo biological tissue on a support; (b) illuminating said in vivo biological tissue with a focused beam of laser light, said light emerging from said in vivo biological tissue comprising fundamental light, harmonic wave light, and fluorescence due to multi-photon excitation; (c) selectively passing only at least one of said harmonic wave light and said fluorescence; (d) individually detecting each of said harmonic wave light and said fluorescence selectively passed; and (e) moving said support relative to said focused beam in x, y and z directions.

According to another aspect of the invention, there is provided an apparatus utilizing non-linear optical signals for use in constructing a tomographic map of a turbid medium, said apparatus comprising (a) means for illuminating said turbid medium with a focused beam of laser light, said light emerging from said turbid medium comprising fundamental light, harmonic wave light, and fluorescence due to multi-photon excitation; (b) means for collecting the light emerging from said turbid medium; (c) means for splitting said collected light into a first beam and a second beam; (d) a first filter disposed along the path of said first beam for selectively passing only said harmonic wave light; (e) a second filter disposed along the path of said second beam for selectively passing only said fluorescence; (f) a first detector disposed along the path of said first beam after said first filter; (g) a second detector disposed along the path of said second beam after said second filter; (h) means for bringing said filtered light of said first beam to focus on said first detector; and (i) means for bringing said filtered light of said second beam to focus on said second detector.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference characters represent like parts:

FIG. 1(a) is a schematic diagram of the focal region of FIG. 1, wherein 3-dimensional scanning is accomplished by moving the objective or by moving the sample (the non-linear signals being generated mostly from the focal region);

DETAILED DESCRIPTION OF PREFERRED EMBODIMENTS

The present invention is based, in part, on the discovery that non-linear optical signals (harmonic generation and multi-photon excitation of fluorescence) can be used as a noninvasive in situ tomography and histology technique to generate 3-dimensional layered structure maps of symmetry and content of native fluorophors in highly scattering biological tissues. Such a 3-dimensional image may be obtained by using depth (z) and lateral (x,y) scans of a highly focused laser beam relative to the tissue sample. Non-linear optical signals are measured and used to resolve symmetry and content properties of layers in biological tissues and thus to image the morphology structure of tissues. One may use these images to distinguish regions on a tissue at different states: normal, benign, pre-cancer, and cancerous states.

As a test of these principles, SHG and TPF signals backscattered from highly scattering biological tissues were used to obtain tomographic images of tissue structures below the surface up to a depth of 500 $\mu$m. The results are discussed below.

Figure 1:
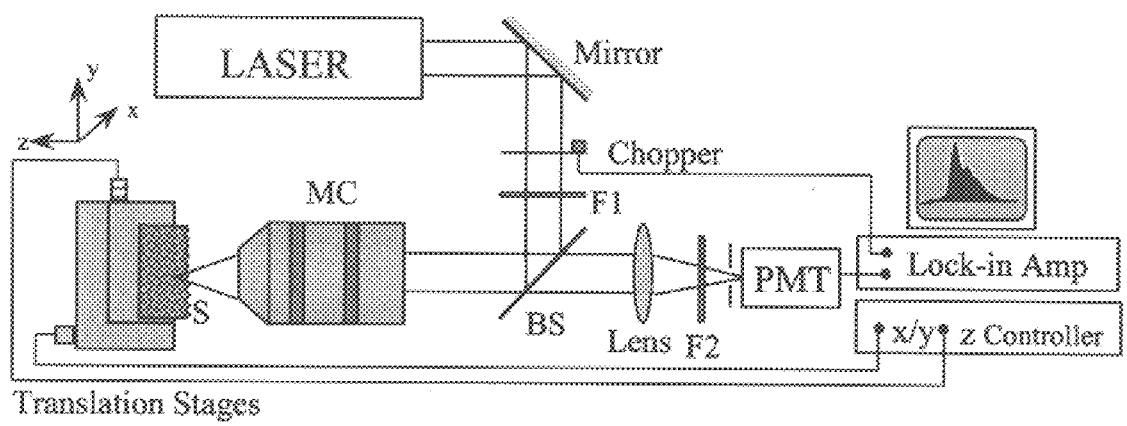
FIG. 1 is a diagrammatic illustration of an experimental setup for testing the non-linear optical imaging concepts of this invention where MC is the microscope objective; F1 and F2 are bandpass filters; PMT is a photomultiplier tube.

An experimental setup used to test the concept of using non-linear optical signals to construct a histology symmetry map and histology chemical components map of tissue is shown in FIG. 1. The laser system used was an amplified CPM dye laser which generated 100 fs pulses centered at a wavelength of 625 nm. The repetition rate of the laser pulses was 6.5 kHz. The average power of laser radiation onto the sample was less than 1 mW. A 27X microscope objective was used to deliver the pump light and to collect the signal. The laser beam was focused into different depths (z) below the tissue surface by scanning the sample along the optical axis of the microscope objective with a translation stage. The focal point is scanned at different depth into the tissue as z is moved (see FIG. 1(a)). The lateral cross surface (x, y direction) scanning is performed with another translation stage. The backscattered signal from focal volume in the sample by the objective was collected by a lens into a photo-detector. A photomultiplier and a computer controlled lock-in amplifier were used to detect the signal and record the data. Appropriate band pass filters were inserted in the excitation and signal paths. The samples for demonstration of imaging were excised frozen then thawed chicken tissues obtained from the upper thigh portion.

Figure 1B:
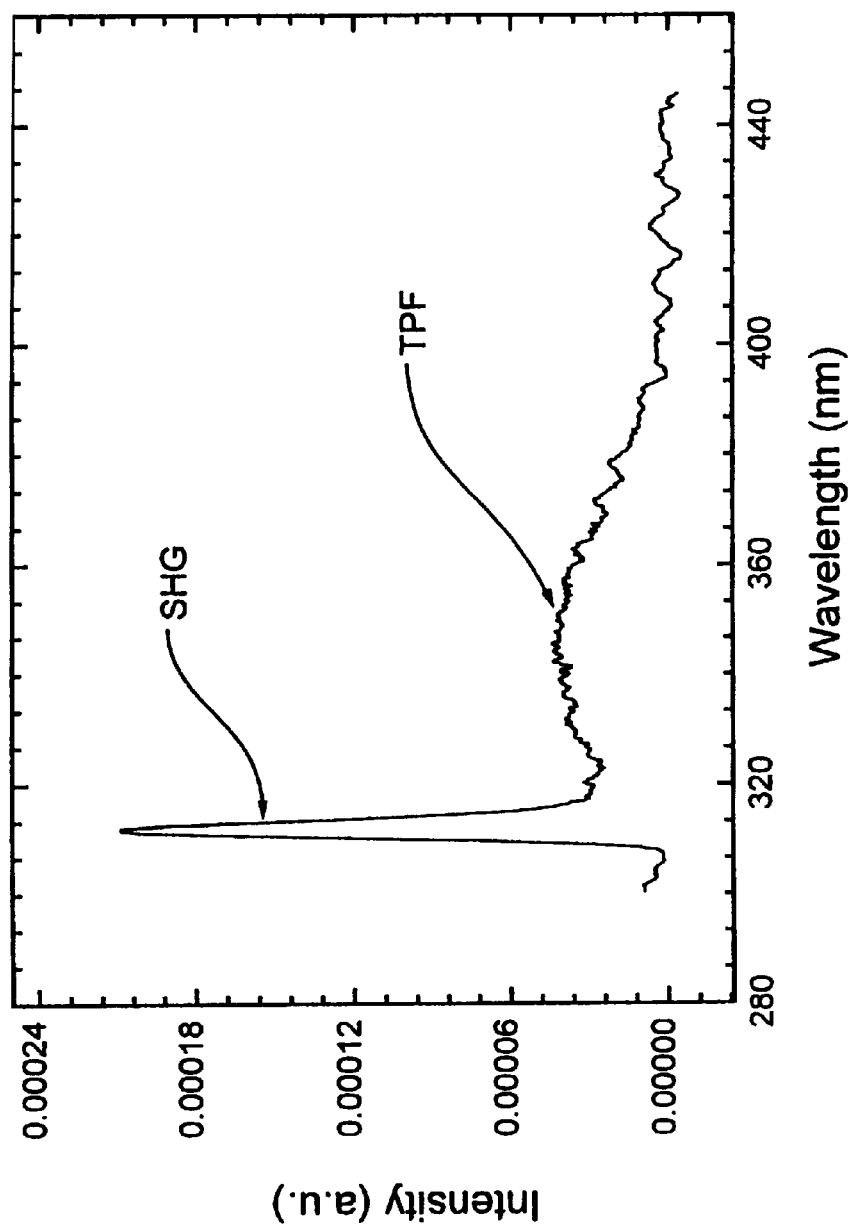
FIG. 1(b) is the graphic representation of the spectrum of non-linear signal from chicken muscle tissue excited by 100 fs laser pulses at a wavelength of 625 nm.

A typical spectrum of non-linear optical signal from chicken muscle tissue excited at 625 nm is shown in FIG. 1(b). This spectrum curve was obtained by replacing the bandpass filter in front of the photo-detector with a spectrometer. The SHG signal at 312.5 nm is larger than the TPF signal from 320 to 400 nm. The TPF signal was determined to be generated from tryptophan molecules in the tissue.

Figure 2:
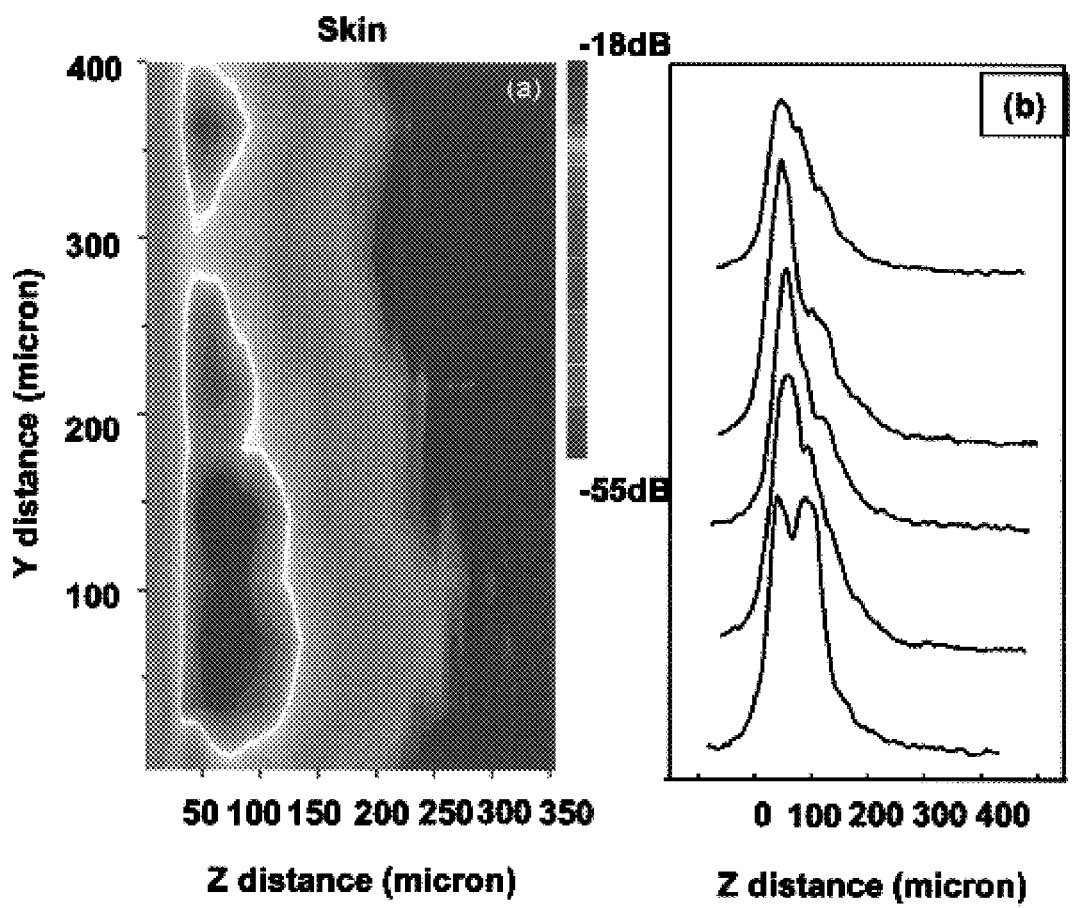
FIG. 2(a) is an SHG depth image of chicken skin tissue.
FIG. 2(b) shows typical axially scanned profiles for the image of FIG. 2(a)
Figure 3:
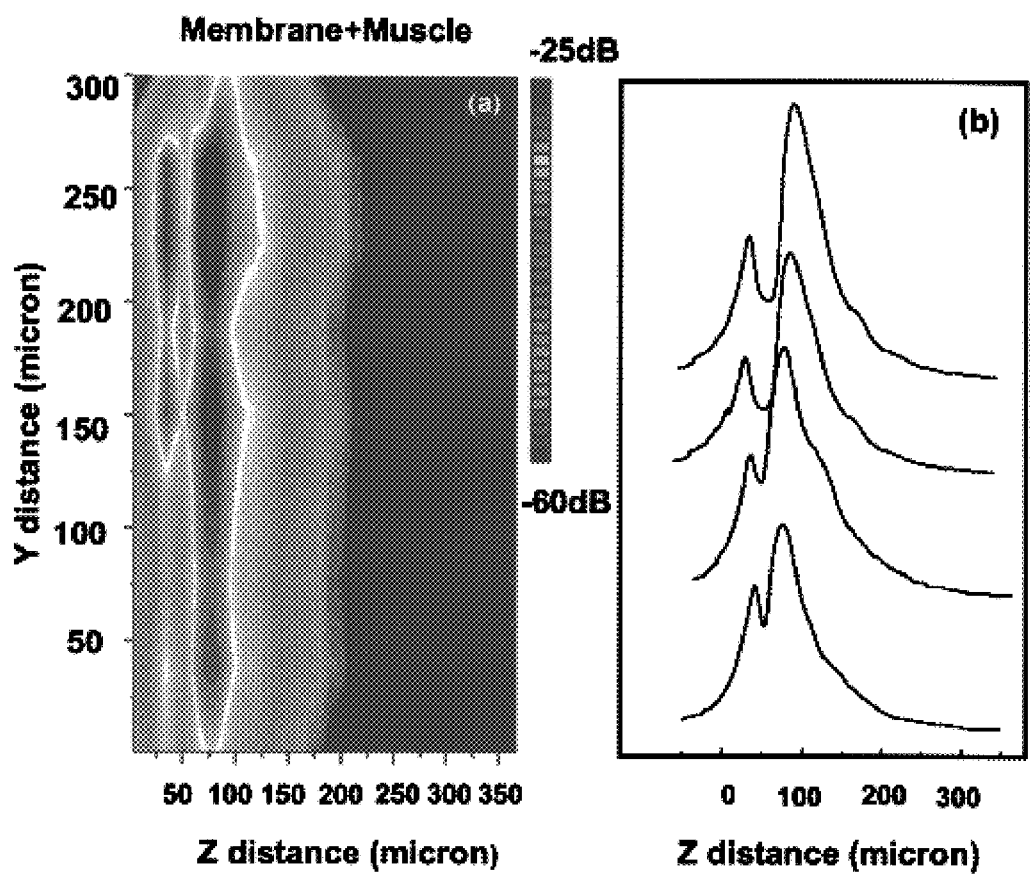
FIG. 3(a) is an SHG depth image of fascia membrane attached to chicken muscle tissue.
FIG. 3(b) shows typical axially scanned profiles for the image of FIG. 3(a)
Figure 4:
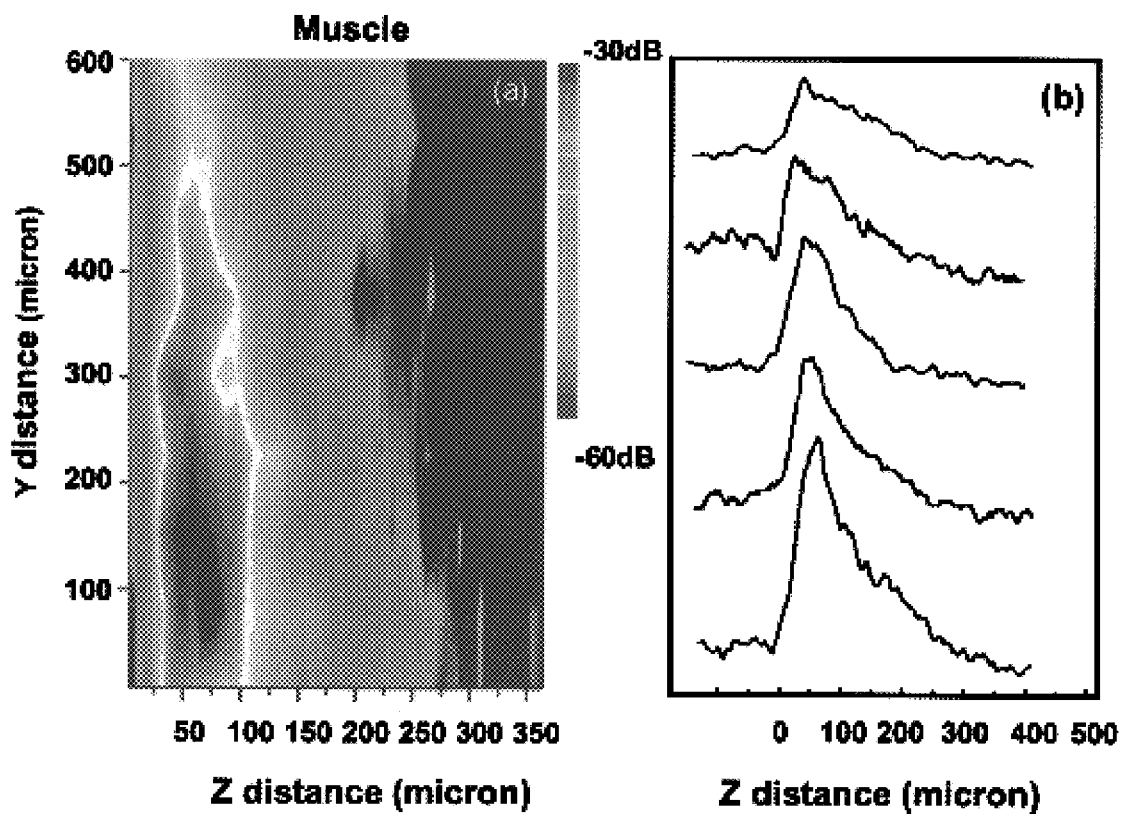
FIG. 4(a) is an SHG depth image of chicken muscle tissue.
FIG. 4(b) shows typical axially scanned profiles for the image of FIG. 4(a)
Figure 5:
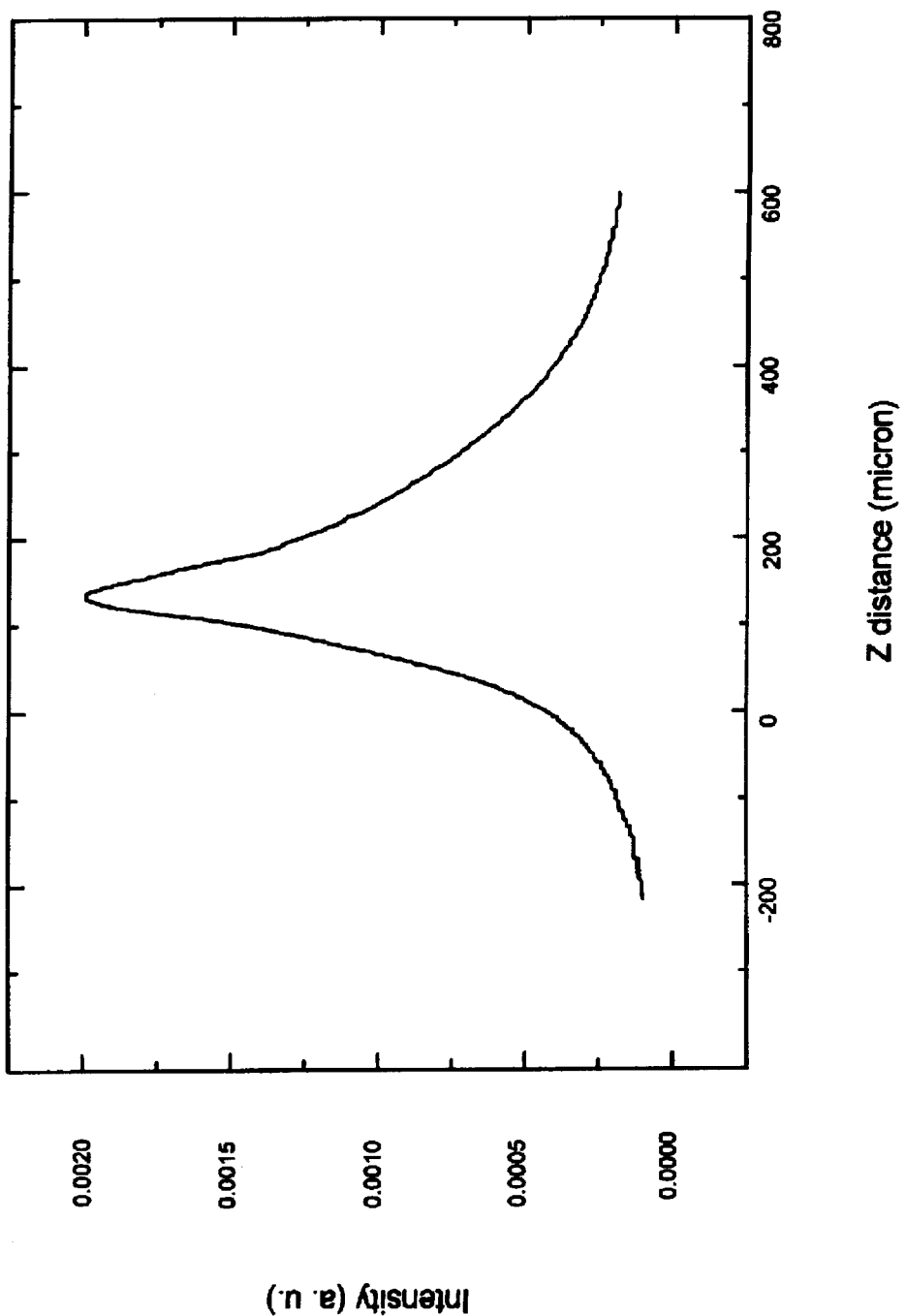
FIG. 5 shows SHG depth profile of tryptophan powders.

Experimental demonstration of the concepts of tomography and histology imaging using SHG and TPF proposed here are shown in FIGS. 2 to 7. 2-dimensional SHG tomography maps (x-z) in pseudo-color from various tissue interfaces are shown in FIGS. 2(a), 3(a) and 4(a). The positive Z direction is defined as the focal plane sliced deeper into the tissue surface. A set of typical axially scanned profiles along the Z direction at different lateral points are displayed in FIGS. 2(b), 3(b), and 4(b). FIG. 2(a) shows the imaged structure of a section of chicken skin tissue attached to a muscle tissue. The map in FIG. 3(a) shows the changes of a tendon like membrane of fascia attached to a muscle tissue. In FIG. 3(a), only muscle tissue was imaged.

The layered structure of the medium is clearly resolved in the SHG profiles scanned in axial direction. The salient features of these profiles are evidenced by the observed intensity apexes along the Z direction, appearing before and after the dominate maximum. In FIG. 2(b), a major peak was resolved first from the skin tissue. The second or the third subsidiary peaks are believed to be resolved from the sub-surface layered structures due to multiple interfaces. In FIG. 3(b), a minor peak emerged first from the tendon membrane, followed by the response from the muscle. The corresponding image in FIG. 3(a) also exhibited two high intensity (red, in some cases yellow) regions with a dip band (green) in between. The first peak was found to have a lower strength and narrower in space if one noticed that a dominant and broader peak appeared first from the skin tissue. An estimation of the membrane thickness is in the range of a few tens of micrometers. In FIG. 4, only muscle tissue has been imaged and the differences can be seen more clearly from the individual axially scanned profiles. In this case, the overall signal is about one order of magnitude smaller than that from the skin tissue, thus the minor changes at the tail part are magnified due to scale differences. From this, one can conclude that the structure is not from a real histology layer, but rather from the detailed variations in the local environment, such as encountered collagen fibrils and mesentery fibers. In order to see the finer structures in FIGS. 3 and 4, we sectioned the image to a corresponding scale. The theoretical depth of the focus was estimated to be ~10 $\mu$m.

To determine whether the observed structure is real, a sample containing a uniformly distributed powder of tryptophan was imaged. As seen in the profile displayed in FIG. 5, the profile is smooth without any fine structures—this confirms that the variations observed in tissue samples are due to difference in local symmetry.

SHG confocal microscopy tomography is a method which combines high spatial resolution with scattering rejection capability and a morphology symmetry sensitivity on a microscopic level. Because the intensity of the harmonic waves are quadratic proportional to the fundamental light intensity, SHG signals are generated from the focal volume in the samples only. The scattered fundamental light, which could be widely distributed in the highly scattering sample, does not generate SHG. Furthermore, detecting SHG in confocal configuration increases collection efficiency. The SHG detected is known coming from focal volume even though SHG light can be scattered when emerging from the sample. Due to symmetry dependence, for example, $\chi^{(2)}$ is inhibited in an isotropic material. However, a broken symmetry occurs at the boundaries which enables a surface SHG contribution. This property has been utilized to probe surface characteristics between liquid and amorphous phases. Compared with the reflectance based imaging technique, SHG has the additional advantage in its symmetry sensitivity. It is not only dependent on the reflectivity or the backscattering coefficient, but it is also a dependent on the $\chi^{(2)}$ tensor, which gives a response that reflects on the morphology symmetry of the ultra-structure.

The reflected signal is given by equation (1):

$$I_{2\omega} \propto 1\beta\pi(\omega/n_{2\omega}c)^2 k S_{2\omega}^2 |\chi_{eff}^{(2)}|^2 I_{1\omega}^2 \qquad (1)$$

where $n_{2\omega}$ is the index of refraction, $S_{2\omega}$ is the backscattering coefficient at $2\omega$, respectively. $\kappa$ is a function related to the particle size. In this way, this process is very different from that of OCT, where the generated signal relies only on the reflectivity (or the backscattering coefficient) of the microstructure in the organism.

SHG image provides additional information regarding to the tissue local symmetry as well as state. SHG tomography can be used to explore the tissue histology in highly turbid medium, since most epithelial abnormalities are associated with morphological distortions, such as Frank cancer and precursors of malignancies. Tissue cells at different states have different symmetry which could lead to differentiable SHG signal strength. SHG may be used to separate out different tissue states, such as cancer, pre-cancer, inflammation, benign, and normal.

Harmonic generation arises from a coherent process where the signal highly depends on the intensity, phase, propagation direction and polarization of the incident primary wave. One of key concerns of various optical imaging in a turbid biomedical medium is to extract measured data at the greatest depths while keeping the focus quality under multiple scattering events. The nature of the optical harmonic generation requires a coherent excitation where the scattering length $l_s$ is the appropriate dimension to characterize the process. The ballistic component carries coherence into the medium. Its intensity depends on the scattering length as $\exp(-z/l_s)$ where z is the penetration length. Within ~ sub-mm of tissue surface, the coherence is still considered to be largely preserved, where the signal is also originated. For measurable SH signals, a depth up to ~ mm is possible depending on the wavelengths. For efficient surface and sub-surface probing using 1200–1300 nm excitation from $Cr^{4+}$:Forsterite laser, the penetration depth into the tissue sample may be up to several mm. This approach indicates a potential for medical diagnosis of epithelia diseases, such as cancer, pre-cancer, sunburns, burns and aging.

Figure 6:
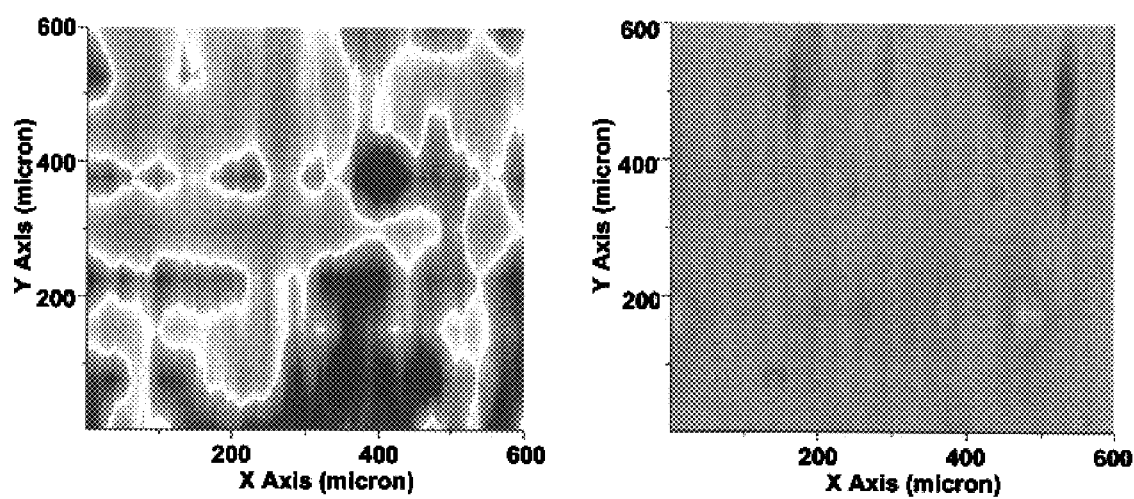
FIG. 6 shows 2D cross section (x-y) TPF images of chicken muscle tissue on (a) surface, and (b) 200 $\mu$m deep inside, the fibers of tissue being aligned mostly along the optical axis (z axis)
Figure 7:
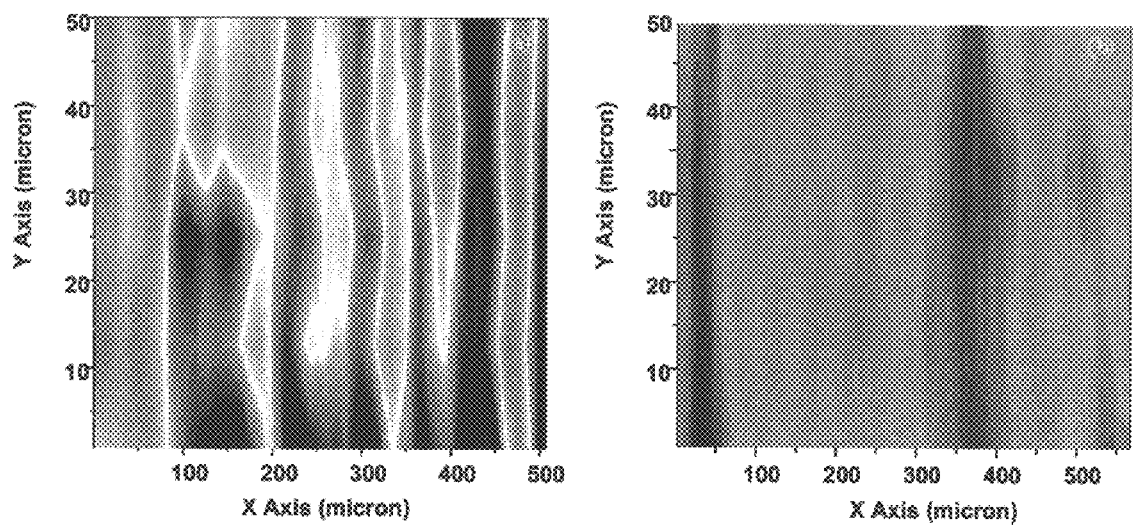
FIG. 7 are 2D images similar to FIG. 6, but wherein the fibers of tissue were aligned mostly perpendicular to the optical axis.

Imaging the molecular makeup of a tissue structure using TPF was achieved using the same experimental setup as SHG imaging except that the bandpass filter in front of the photo-detector was changed to one passing through fluorescence of trypotophan from 320 to 400 nm while rejecting the SHG at 310 nm. Measurements were performed on a chicken muscle tissue. FIGS. 6 and 7 show tomographic images of tryptophan structure in a chicken muscle tissue sample at a fixed depth, i.e., x-y images. FIG. 6 shows the result when tissue fibers were aligned mostly along the optical axis. The image clearly shows the round shape of individual tissue fiber. FIG. 7 shows the image when the tissue fiber is aligned mostly perpendicular to the optical axis. The image clearly shows the line shape of fibers.

Figure 8:
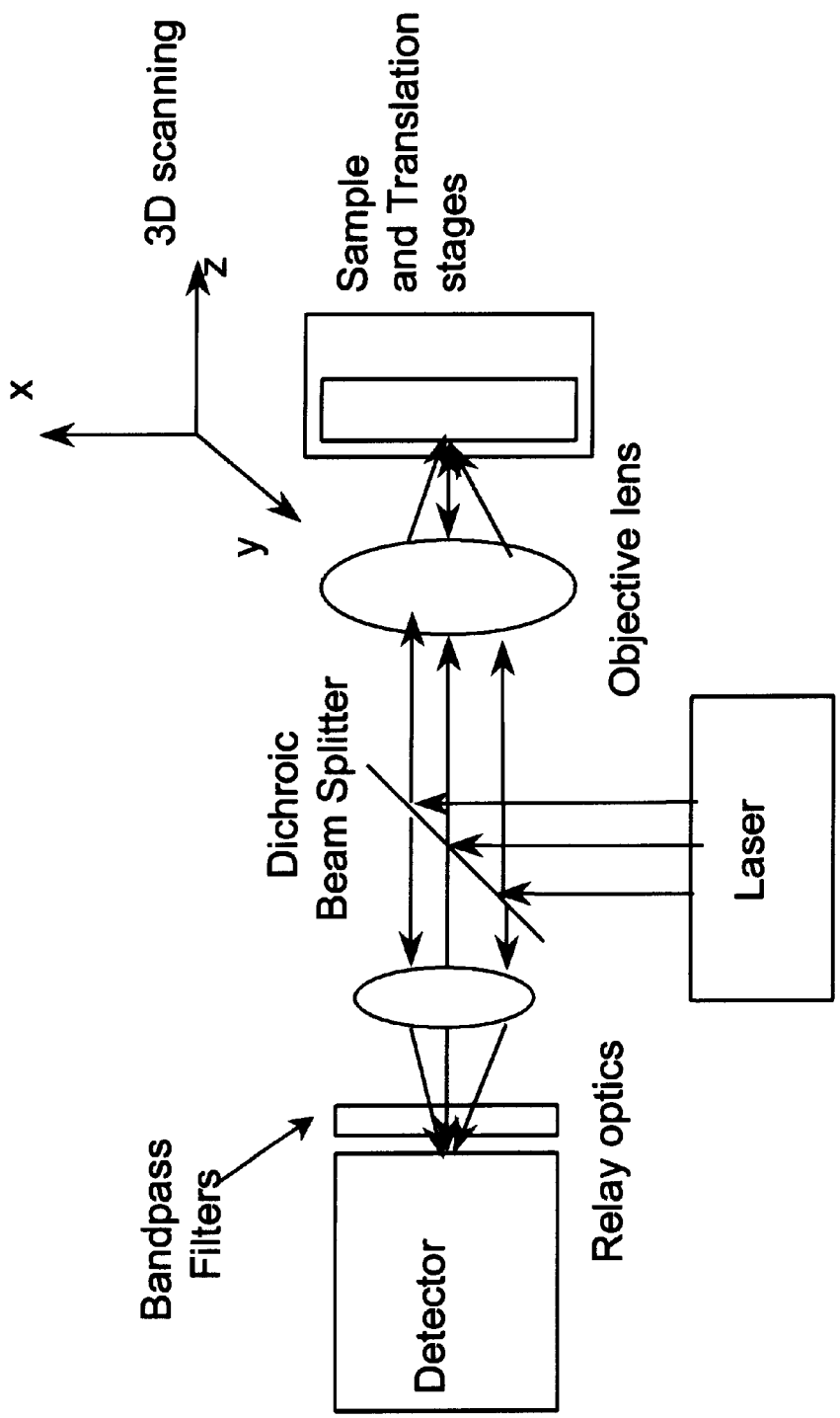
FIG. 8 is the input and detection optics arrangement for one embodiment of the invention.
Figure 8A:
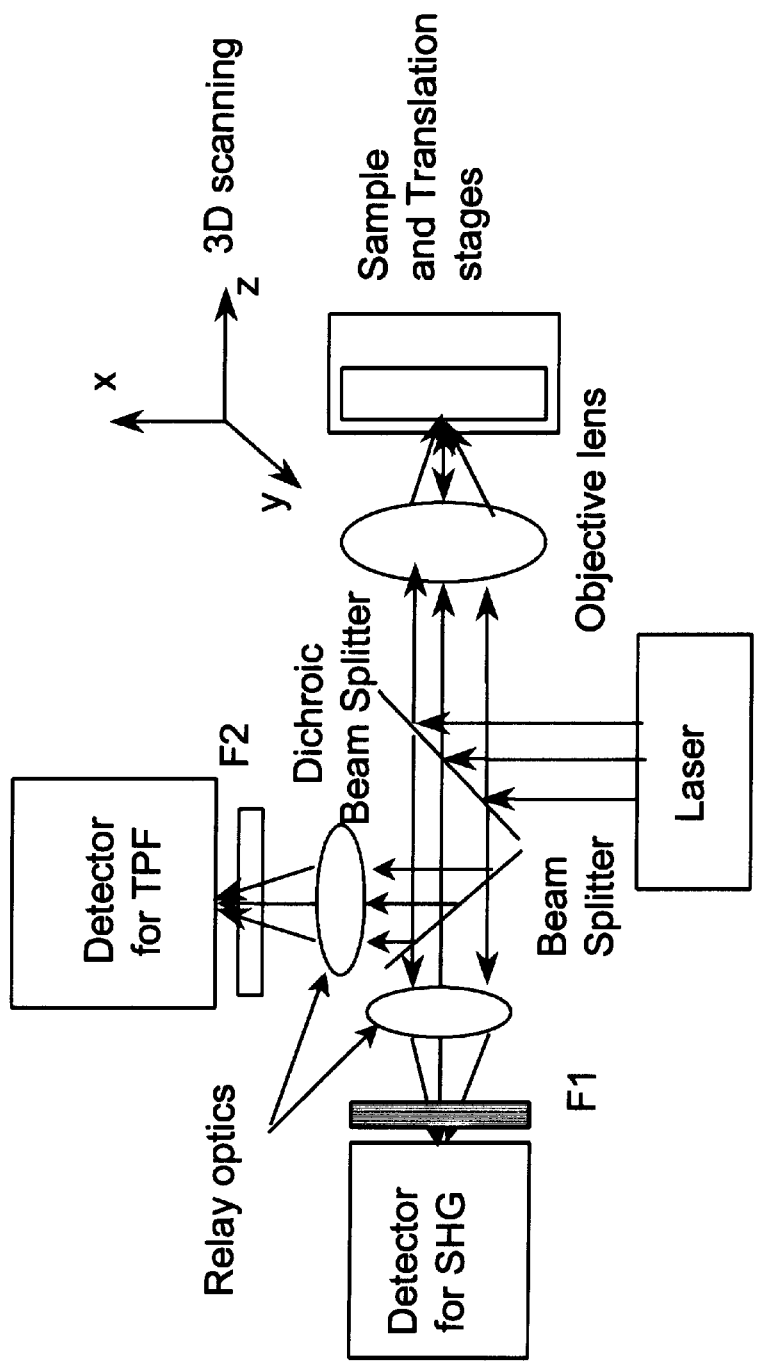
FIG. 8(a) is the input and detection optics arrangement for another embodiment of the invention.
Figure 9:
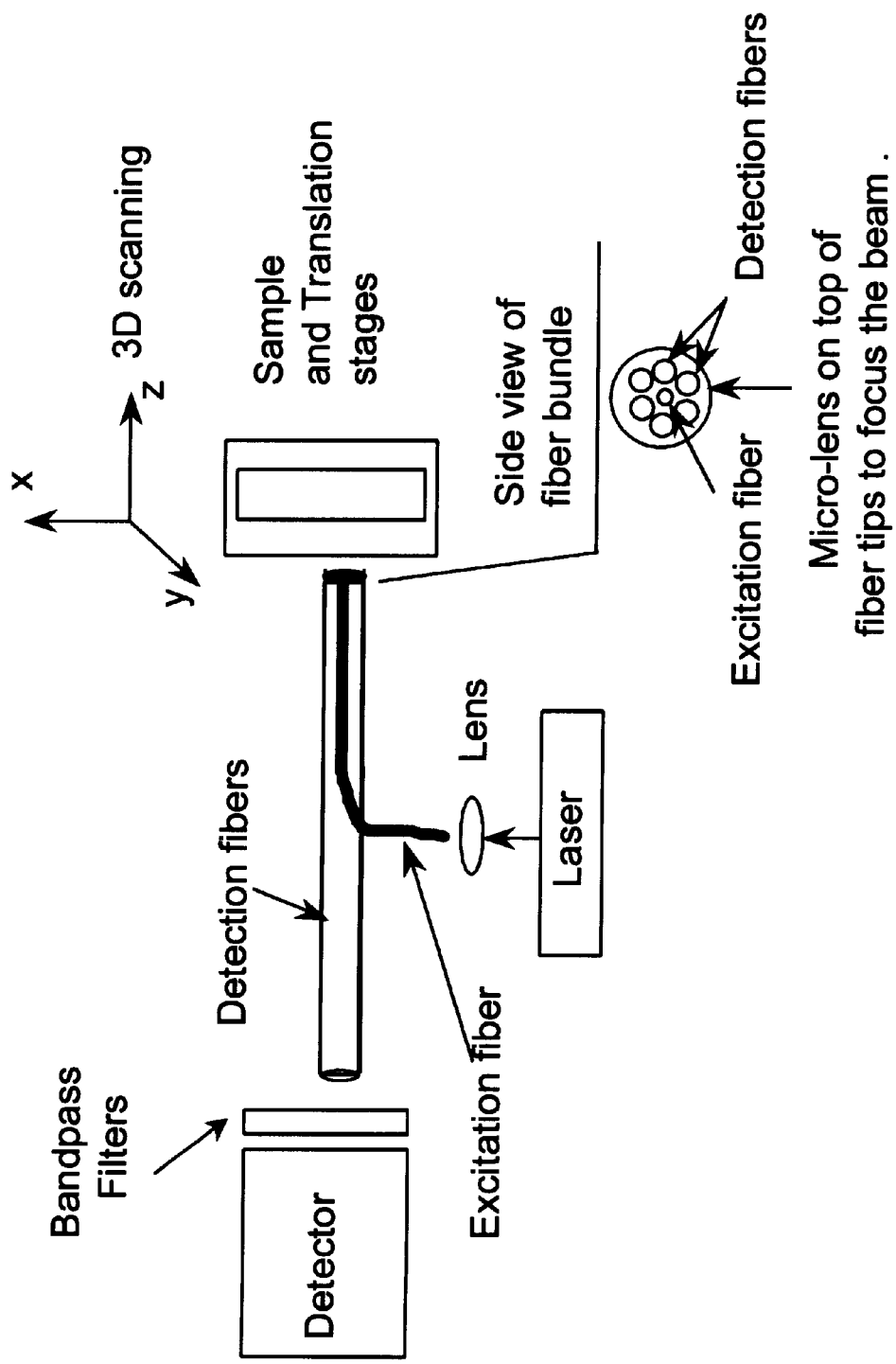
FIG. 9 is the input and detection optics arrangement for yet another embodiment of the invention.

The TPF images shown above (FIGS. 6 and 7) are tomographic maps of tryptophan distribution in the tissue. By selecting different pass band optical filters or using a spectrograph, multiple-photon excitation of fluorescence and harmonic generation from samples can be detected to obtain a 3-D image of the symmetry structure and molecular chemical contents of the sample. Non-linear optical signals at different wavelength from spatial point on the sample could provide more useful information, such as symmetry and molecular chemical constituents, about the sample than detecting signal from single wavelength band. Using excitation at different wavelengths, spatial distribution of different native molecules (fluorophors) such as elastin, flavins, collagen, and NADH, can be imaged. Table 1 summarizes the spectroscopy properties of common native fluorophors in tissue. Excitation and fluorescence wavelengths of important native fluorophors, and types of ultrashort pulse lasers to be used for non-linear optical imaging them are listed in Table 1.

in FIGS. 8 through 11. FIG. 8 shows an experimental setup with a backscattering geometry. The laser beam is directed to the sample by a dichroic beam splitter and a microscope objective. The dichroic beam splitter reflects the excitation laser light from the laser and from the sample while transmitting the SHG and TPF light generated from tissue sample. The MPEF and HG from the tissue sample were collected by the same objective and transmitted through the dichroic beam splitter. The non-linear optical signal was then collected by relay optics, passed through a filter selective for the desired light (i.e., HG or MPEF) and impinged on a photo-detector. The signals detected by the photo-detector may then be recorded, processed and displayed by a computer (not shown). The scanning is accomplished by moving the sample using translation stages. This type of the setup was used in the demonstration of the principles shown above. FIG. 9 shows the schematic for incorporating an optical fiber into the imaging system. Laser light is coupled into a fiber in a fiber bundle. A micro-lens at the end of bundle tip is used to focus light into the tissue sample. The non-linear optical signals are collected by other fibers in the bundle and relayed to a photo-detector. Quartz fibers are to be used to deliver the laser light to the sample and to collect non-linear optical signals. This design may be used for

TABLE 1

Spectroscopy properties of important common native fluorophors in tissue and laser sources to be used for SHG and TPF imaging

| NATIVE FLUOROPHORS IN TISSUE (TISSUE FINGER PRINTS) | EXCITATION WAVELENGTH BAND | EMISSION WAVELENGTH BAND | LASER SOURCE FOR SHG AND TPF IMAGING |
| --- | --- | --- | --- |
| Trypotophan | 280 nm | 340 nm | 560~630 nm, Dye, Forsterite(SHG) |
| Collagen | 340 nm | 380 nm | 680~700 nm, Dye, Ti:Sapphire, Cr:YAG(SHG) |
| Elastin | 360 nm | 410 nm | 700~740 nm, Dye, Ti:Sapphire, Cr:YAG(SHG), CUNYITE(SHG), |
| Flavins | 450~460 nm | 525 nm | 900~940 nm, Dye, Ti:Sapphire |
| NADH | 360 nm | 460 nm | 700~730 nm, Ti:Sapphire, Dye, CUNYITE(SHG), Cr: YAG(SHG) |
| Proteins | 250~280 nm | 300~350 nm | 500~560 nm, Nd:YAG(SHG) |
| Porphyrins | 600~700 nm | 630~800 nm | 1200–1400 nm, CUNYITE, Forsterite |

The laser sources to be used include short pulse generate fundamental wavelength as well as second-harmonic waves generated from the laser. For example, Nd:YAG laser generates picosecond duration 1064 nm fundamental light pulses as well as 532 nm SHG light pulses. Images of chemical makeup and symmetry properties of tissue sample could lead to the determination of the state and histology of tissue. Non-linear optical images can be used to locate cancer, pre-cancer, and normal region in a tissue. The spatial resolution non-linear optical tomography is comparable to microscopy and OCT. By selecting the fundamental wavelength in the infrared region, the focus quality and depth of penetration can be further improved to circumvent multiple scattering and absorption effects. Non-linear optical scanning imaging techniques can also be implemented with fiber optics and is adaptable to endoscopy for morphology evaluation inside the human and animal bodies.

Figure 10:
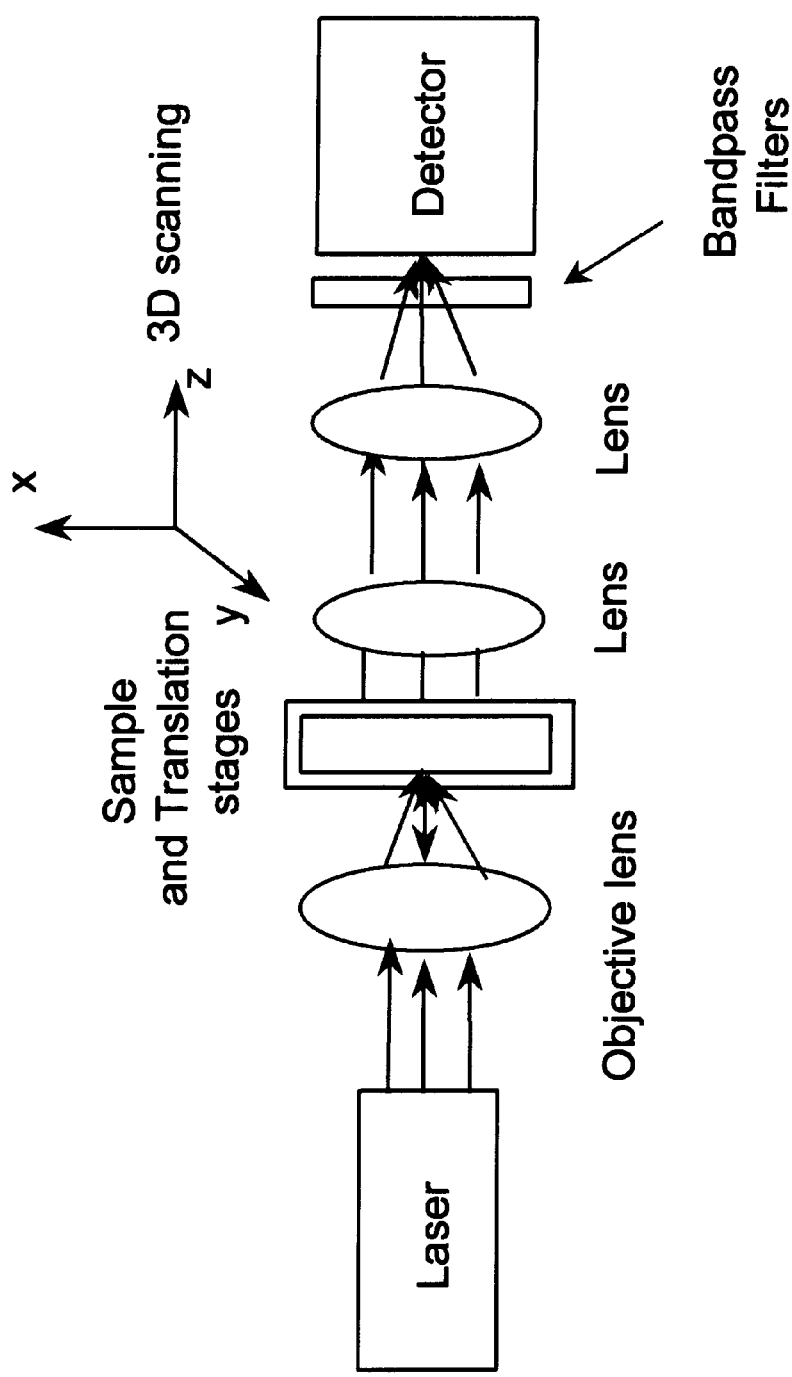
FIG. 10 is the input and detection optics arrangement for still another embodiment of the invention.
Figure 11:
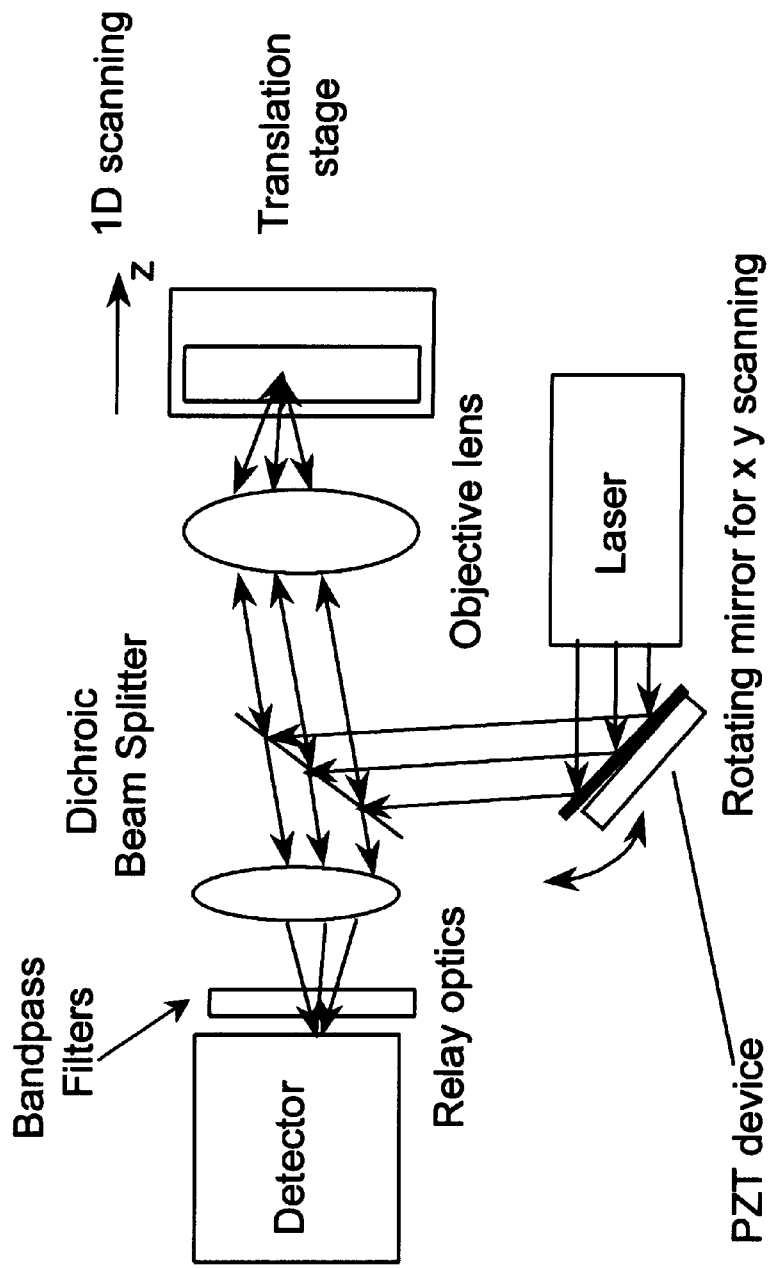
FIG. 11 is the input and detection optics arrangement for still yet another embodiment of the invention.
Figure 11A:
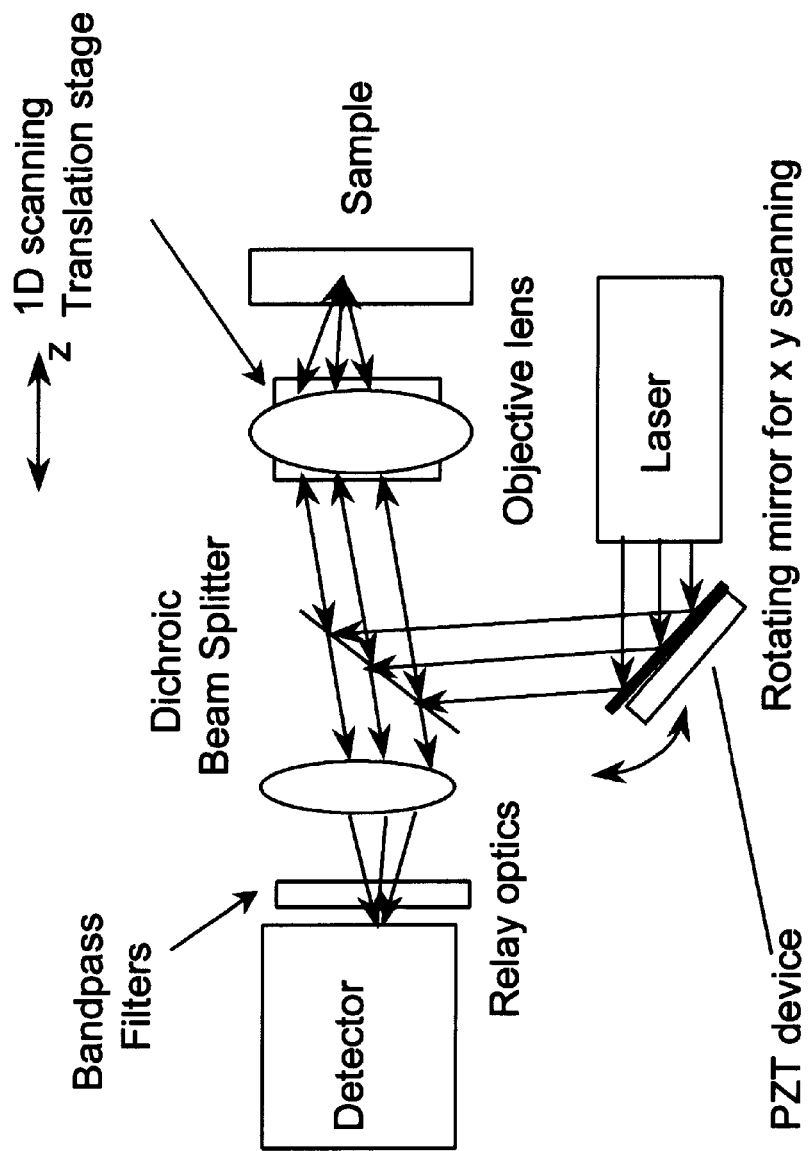
FIG. 11(a) is the input and detection optics arrangement for a further embodiment of the invention.

Schematics of different experimental arrangements proposed to perform non-linear optical tomography are shown endoscopy applications. FIG. 10 shows the setup for a transmission geometry. Laser light is delivered to the sample by a microscope objective lens. The transmitted nonlinear optical signal is collected by optics and detected by a photo-detector. This design is suitable for thin samples or near-transparent samples. The scanning is accomplished by moving the sample. FIG. 11 shows the experimental arrangement of using rotating optics to achieve x-y scanning. The rotation is controlled by galvanometer and/or PZT devices. The depth scan is controlled by moving the sample. The detector shown in these schematics includes components separating the non-linear optical signal from the excitation light, and components detecting the non-linear optical signals.

Figure 12:
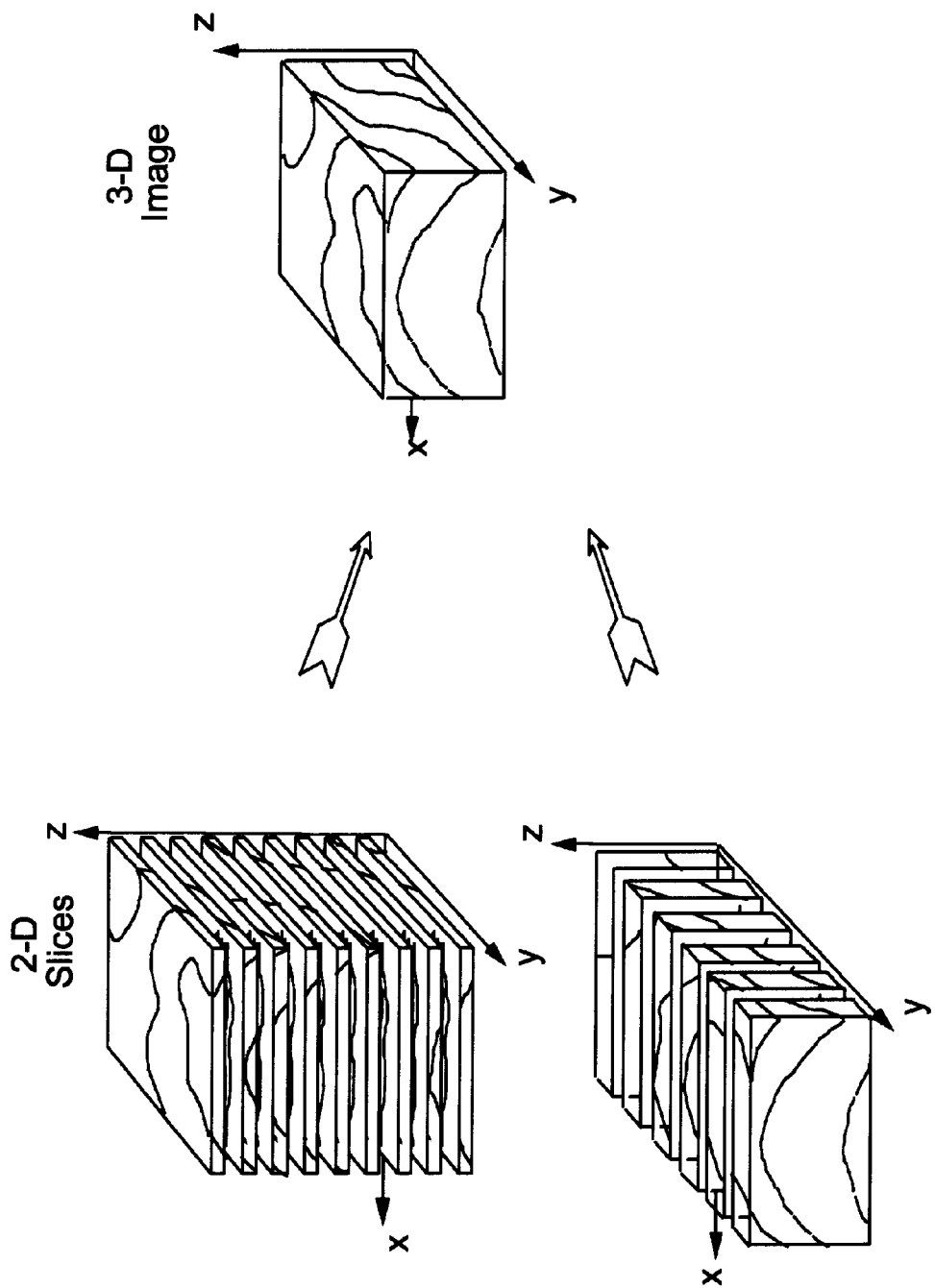
FIG. 12 is a schematic diagram combining 2D tomographic maps into a 3D map of tissue sample according to this invention.

The SHG and TPF images shown above for the demonstration of the principles are 2-D images. The images are tomographic slices of the tissue sample. 3-D images can be obtained by combining these 2-D images together for better visualization. As shown in FIG. 12, x-y slices at different depths z or x-z images at different lateral positions y can be combined to form a 3-D image. Interested volumes in the sample can then be easily identified.

The nonlinear techniques shown here not only can be used for imaging structures of interested medium, but also can be used to induce a precision local change inside the medium. Multi-photon absorption and induced fluorescence, as well as harmonic generation, can be used to activate dyes used in photodynamic therapy (PDT) and to induce photopolymerization for microfabrification.

The following are various uses, features, descriptions, advantages, aspects and objects of the present invention, said uses, features, descriptions, advantages, aspects and objects not intended to be limiting:

(1) A tomographic histology imaging system for scattering/turbid medium and biomedical tissues comprises:
- illuminating the medium with a pulsed laser light source using input optics,
- the light emerging therefrom consisting the fundamental (incident) light and the harmonic wave light, and fluorescence due to multi-photon excitations(MPEF),
- collecting the harmonic wave signals and fluorescence (MPEP) generated in the medium using optics, detecting the collected harmonic wave signals with a photo-detector, means of 3-dimentional (x, y, z) scanning the beam and/or sample medium, means of detecting the signal at different spatial position of the medium,
- displaying the detected signal as a function of position of the medium to obtain tomography maps in different section of the medium and 3-dimentional maps of the medium.

(2) The system of paragraph (1), wherein said pulsed laser light source are pulsed lasers generating picosecond and femtosecond fundamental and second harmonic light pulses in 400~1400 nm wavelength region.

The NIR mode-locked lasers include Ti:Sapphire, $Cr^{4+}$:Forsterite, Nd:YAG, Cr:YAG, $Cr^{4+}:Ca_2GeO_4$(CUNYITE), Colliding pulse mode-lock lasers, and semiconductor diode lasers.

Laser pulses at longer wavelength (>600 nm) can be used for deeper scanning into the tissue sample.

Laser pulses at different wavelengths are used to excite different components of tissues. Table 1 shows the laser to be used for probing different components of tissues. For example, TPF excited from 540 to 630 nm fundamental light is mostly generated from trypotophan molecules, while TPF excited from 630 to 700 nm mostly comes from collagen, and elastin.

(3) The system of paragraph (1), wherein said input optics comprises a dichroic beam splitter, a microscope objective lens, and beam directing mirrors. The detecting optics comprises the same microscope objective lens and relay optics to send optical signal to a detector. See FIG. 8.

(4) The system of paragraph (1), wherein said input optics comprises an optical fiber bundle, a lens coupling laser source to a single fiber in the bundle. The optical signal is detected by other fibers of the bundle and relay to detector. At the end of bundle, micro-lens is to be attached to focus the beam into the sample. See FIG. 9.

(5) The system of paragraph (1), wherein said input optics comprises a microscope objective, and the detection optics comprises lenses in transmission mode. This design is suitable for near-transparent samples or thin highly scattering samples. See FIG. 10.

(6) The photo-detector comprises band pass filters at harmonic wave and MPEF wavelengths to reject the scattered laser light collected by the optics, and a photomultiplier, a CCD camera, or an intensified CCD camera.

(7) The photo-detector comprises a spectrograph to select harmonic wave signals and MPEF at the same time, an arrayed photodetector, a CCD camera, or an intensified CCD camera.

(8) The scanning system of paragraph (1) comprises a platform to mount the sample medium. The platform is mounted on a 3-axis translation stage. The sample is scanned. The movement of the stages is controlled by a PC computer.

(9) The scanning system of paragraph (1) comprises a platform mounting the sample, the platform being mounted on a single axis translation stage to perform depth scan by moving the focal point into the sample. The transverse scan (x,y scan) is accomplished by adding a rotating mirror or a beam deflector to the input optics. The rotation is controlled by galvanometer and/or PZT (piezoelectric) device. See FIG. 11. This design can also be incorporated in the system of paragraph (5).

(10) The scanning system of paragraph (1) comprises a platform to mount the input optics. The platform is mounted on a translation or rotational stage to scan the input beam. The sample medium is kept fixed. The movement of the stage is controlled by a PC computer.

(11) The scattering and/or turbid media may be, for example, human skin, human cervix and vagina, human gastrointestinal tract, human prostate and human bladder.

(12) Use of SHG image obtained from the system of paragraph (1) to obtain information on local symmetry properties of tissue surface and regions inside the tissues up to a few mm.

(13) Use of MPEF at different excitation wavelengths to obtain histology maps of tissue native fluorophor components, such as tryptophan, elastin, collagen, flavins, porphyrins, and NADH.

(14) Combine harmonic wave images and MPEF images from native proteins and molecules on the surface and a few mm inside tissues to obtain a chemical and symmetry makeup of the tissue.

(15) Use of harmonic wave and MPEF images to distinguish normal and pre-cancer, cancer tissues. Use of images for diagnosis of inflammation, burns, aging.

(16) Use TPF to produce images to distinguish cancer, pre-cancer, benign, and normal regions of tissue.

(17) Use SHG to produce images to distinguish cancer, pre-cancer, benign, and normal regions of tissue.

(18) To produce 2D and 3D difference and/or ratio image maps using SHG images of tissues obtained by different excitation wavelengths from tunable mode-locked laser. The difference and/or ratio maps are to be used to determine the states of tissue: cancer, pre-cancer, benign, and normal.

(19) To produce 2D and 3D difference and/or ratio maps using TPF images of tissues obtained by different excitation wavelengths from tunable mode-locked laser and their second harmonic beams. See FIG. 12 and Table 1. The difference and/or ratio maps are to be used to determine the states of tissue: cancer, pre-cancer, benign, and normal.

(20) To produce 2D and 3D difference and/or ratio maps using SHG images of tissues obtained at different detection wavelengths. The difference and/or ratio maps are to be used to determine the states of tissue: cancer, pre-cancer, benign, and normal.

(21) To produce spectral SHG maps of tissue highlighting different chemical components of tissue: tryptophan, collagen, elastin, NADH, porphyrins, and flavins.

(22) To produce spectral TPF maps of tissue highlighting different chemical components of tissue: tryptophan, collagen, elastin, NADH, porphyrins, and flavins.

(23) Using images obtained from the systems of paragraphs 21 and 22 for separating cancer, pre-cancer, benign legions from normal legions.

(24) Using inherent high magnification of SHG images to yield symmetry properties of cells at different stage of deformation for diagnosing disease at early stages.

(25) Using TPF image to yield component makeup of cells for diagnosing disease at different stages.

(26) Using SHG to detect distortion of cells in cell smears and PAP for detecting cervix, vagina, and lung cancer.

(27) Using SHG and TPF image for in situ disease diagnosis of tissue.

(28) Use of SHG and TPF imaging techniques with endoscope and optical fibers for remote investigation inside the body.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An apparatus for use in constructing a three-dimensional tomographic map of a sample, said apparatus comprising:
   (a) means for scanning the sample with a focused beam of laser light in x, y and z directions, said light emerging from the sample comprising fundamental light, at least second-order harmonic wave light, and fluorescence due to multi-photon excitation;
   (b) means for selectively passing only said at least second-order harmonic wave light and said fluorescence due to multi-photon excitation;
   (c) means for individually detecting each of said at least second-order harmonic wave light and said fluorescence due to multi-photon excitation selectively passed; and
   (d) means for generating a three-dimensional tomographic map of the sample using the light detected by said detecting means.

2. The apparatus as claimed in claim 1 wherein said scanning means comprises a laser and wherein said laser and said selectively passing means are arranged in a backscatter geometry.

3. The apparatus as claimed in claim 1 wherein said scanning means comprises a laser and wherein said laser and said selectively passing means are arranged in a transmission geometry.

4. The apparatus as claimed in claim 1 wherein said scanning means comprises a laser and an optical fiber, said optical fiber having an input end coupled to the output from said laser.

5. The apparatus as claimed in claim 1 wherein said scanning means comprises a laser for illuminating the sample with fundamental and second-harmonic laser light pulses, said fundamental laser light pulses having a wavelength in the range of approximately 400–1400 nm.

6. The apparatus as claimed in claim 5 wherein said laser is selected from the group consisting of Ti:Sapphire, $Cr^{4+}$:Forsterite, Nd:YAG, Cr:YAG, $Cr^{4+}$:$Ca_2GeO_4$, colliding pulse mode-lock, and semiconductor diode lasers.

7. The apparatus as claimed in claim 5 wherein said scanning means further comprises a stage, the sample being mounted on said stage, said stage being movable in the x, y and z directions.

8. The apparatus as claimed in claim 7 wherein said scanning means further comprises an optical fiber, said optical fiber having an input end coupled to the output from said laser.

9. The apparatus as claimed in claim 5 wherein said scanning means further comprises means, optically coupled to the output of said laser, for causing the output of said laser to scan in the x and y directions and a stage, the sample being mounted on said stage, said stage being movable in the z direction.

10. The apparatus as claimed in claim 9 wherein said means for causing the output of said laser to scan in the x and y directions comprises a rotating mirror.

11. The apparatus as claimed in claim 1 wherein said selectively passing means comprises band pass filters selective for said at least second-order harmonic wave light and said fluorescence due to multi-photon excitation.

12. The apparatus as claimed in claim 1 wherein said detecting means comprises a pair of detectors, each of said detectors being a detector selected from the group consisting of a photomultiplier, a CCD camera and an intensified CCD camera.

13. The apparatus as claimed in claim 1 wherein said selectively passing means comprises a spectrograph and wherein said detecting means comprises an arrayed photodetector, a CCD camera and an intensified CCD camera.

14. A method for constructing a three-dimensional tomographic map of a sample, said method comprising the steps of:
   (a) scanning the sample with a focused beam of laser light in x, y and z directions, said light emerging from the sample comprising fundamental light, at least second-order harmonic wave light, and fluorescence due to multi-photon excitation;
   (b) selectively passing only said at least second-order harmonic wave light and said fluorescence due to multi-photon excitation;
   (c) individually detecting each of said at least second-order harmonic wave light and said fluorescence due to multi-photon excitation selectively passed; and
   (d) generating a three-dimensional tomographic map of the sample using the light detected.

15. The method as claimed in claim 14 wherein the sample is a biological tissue sample.

16. The method as claimed in claim 15 wherein the sample is an in vivo biological tissue sample.

17. The method as claimed in claim 15 wherein the sample is an in vitro biological tissue sample.

18. The method as claimed in claim 15 wherein the sample is a biological tissue sample obtained from a part of the body selected from the group consisting of the skin, the cervix, the vagina, the gastrointestinal tract, the prostate and the bladder.

19. The method as claimed in claim 15 wherein the biological tissue sample has no extrinsic fluorophors added thereto.

20. The method as claimed in claim 15 wherein said three-dimensional tomographic map also maps the carcinomatoid state of the biological tissue sample.

21. The method as claimed in claim 14 wherein said scanning step comprises illuminating the sample using a laser emitting fundamental and second-harmonic laser light pulses, said fundamental laser light pulses having a wavelength in the range of approximately 400–1400 nm.

22. The method as claimed in claim 21 wherein said scanning step comprises illuminating the sample using a laser emitting fundamental and second-harmonic laser light pulses, said fundamental laser light pulses having a wavelength in the range of about 560–630 nm.

23. The method as claimed in claim 21 wherein said scanning step comprises illuminating the sample using a laser emitting fundamental and second-harmonic laser light pulses, said fundamental laser light pulses having a wavelength in the range of about 680–700 nm.

24. The method as claimed in claim 21 wherein said scanning step comprises illuminating the sample using a laser emitting fundamental and second-harmonic laser light pulses, said fundamental laser light pulses having a wavelength in the range of about 700–740 nm.

25. The method as claimed in claim 21 wherein said scanning step comprises illuminating the sample using a laser emitting fundamental and second-harmonic laser light pulses, said fundamental laser light pulses having a wavelength in the range of about 900–940 nm.

26. The method as claimed in claim 21 wherein said scanning step comprises illuminating the sample using a laser emitting fundamental and second-harmonic laser light pulses, said fundamental laser light pulses having a wavelength in the range of about 700–730 nm.

27. The method as claimed in claim 21 wherein said scanning step comprises illuminating the sample using a laser emitting fundamental and second-harmonic laser light pulses, said fundamental laser light pulses having a wavelength in the range of about 500–560 nm.

28. The method as claimed in claim 21 wherein said scanning step comprises illuminating the sample using a laser emitting fundamental and second-harmonic laser light pulses, said fundamental laser light pulses having a wavelength in the range of about 1200–1400 nm.

29. The method as claimed in claim 14 wherein said scanning and selectively passing steps are performed using a transmission geometry.

30. The method as claimed in claim 14 wherein said scanning and selectively passing steps are performed using a backscattering geometry.

31. The method as claimed in claim 14 wherein said scanning step comprises mounting the sample on a stage, said stage being movable in the x, y and z directions, and illuminating the sample while moving said stage in the x, y and z directions.

32. The method as claimed in claim 14 wherein the sample is mounted on a stage, said stage being movable in the z direction, and wherein said scanning step comprises illuminating the sample with a scanning beam in the x and y directions while moving the stage in the z direction.

33. An apparatus for use in constructing a tomographic map of a turbid medium, said apparatus comprising:
(a) means for illuminating said turbid medium with a focused beam of laser light, said light emerging from said turbid medium comprising fundamental light, at least second-order harmonic wave light, and fluorescence due to multi-photon excitation;
(b) means for collecting the light emerging from said turbid medium;
(c) means for splitting said collected light into a first beam and a second beam;
(d) a first filter disposed along the path of said first beam for selectively passing only said at least second-order harmonic wave light;
(e) a second filter disposed along the path of said second beam for selectively passing only said fluorescence due to mutli-photon excitation;
(f) a first detector disposed along the path of said first beam after said first filter;
(g) a second detector disposed along the path of said second beam after said second filter;
(h) means for bringing said filtered light of said first beam to focus on said first detector;
(i) means for bringing said filtered light of said second beam to focus on said second detector; and
(j) means for generating a tomographic map using the light detected by said first and second detectors.

34. An apparatus utilizing non-linear optical signals for use in constructing a three-dimensional tomographic map of a biological tissue for medical disease detection purposes, said apparatus comprising:
(a) means for supporting said biological tissue;
(b) means for illuminating said biological tissue with a focused beam of laser light, said light emerging from said biological tissue comprising fundamental light, at least second-order harmonic wave light, and fluorescence due to multi-photon excitation;
(c) detector means;
(d) means for collecting said emergent light and bringing said collected light to focus on said detector means;
(e) filter means disposed between said detector means and said collecting means for selectively passing only said at least second-order harmonic wave light;
(f) a 1-dimensional scanning translation stage for supporting said collecting means; and
(g) a PZT device or scanning galvanometer for x-y scanning of said focused beam.

35. The apparatus as claimed in claim 1 wherein the sample is a biological tissue sample and wherein said mapping means also comprises means for mapping the carcinomatoid state of the biological tissue sample.

36. An apparatus for use in constructing a three-dimensional tomographic map of a sample, said apparatus comprising:
(a) a pulsed laser for generating a beam of laser pulses along a first path;
(b) a dichroic beam splitter disposed along said first path for reflecting said beam of laser pulses along a second path and for selectively transmitting non-fundamental light from the sample, said sample being disposed along said second path;
(c) focusing means disposed along said second path for focusing said beam of laser pulses onto the sample, the light emerging from the sample comprising fundamental light, at least second-order harmonicwave light and fluorescence due to multi-photon excitation;
(d) a stage movable in x, y and z directions, the sample being mounted on said stage;
(e) means for detecting each of said at least second-order harmonic wave light and said fluorescence due to multi-photon excitation; and
(f) means for generating a three-dimensional tomographic map of the sample using the light detected by said detecting means.

37. An apparatus for use in constructing a three-dimensional tomographic map of a sample, said apparatus comprising:
(a) a pulsed laser for generating a beam of laser pulses along a first path;
(b) means, disposed along said first path, for causing said beam of laser pulses to scan in x and y directions along a second path;
(c) a dichroic beam splitter disposed along said second path for reflecting said scanning beam of laser pulses along a third path and for selectively transmitting non-fundamental light from the sample, said sample being disposed along said third path;

(d) focusing means disposed along said third path for focusing said scanning beam of laser pulses onto the sample, the light emerging from the sample comprising fundamental light, at least second-order harmonicwave light and fluorescence due to multi-photon excitation;

(e) a stage movable in the z direction, the sample being mounted on said stage;

(f) means for detecting each of said at least second-order harmonic wave light and said fluorescence due to multi-photon excitation; and (g) means for generating a three-dimensional tomographic map of the sample using the light detected by said detecting means.

* * * * *